United States Patent [19]

Cohen et al.

[11] Patent Number: 5,441,961
[45] Date of Patent: Aug. 15, 1995

[54] SUBSTITUTED CYCLO OR BICYCLOALKYLAMIDES OF (8β)-6-(SUBSTITUTED) ERGOLINES

[75] Inventors: Marlene L. Cohen, Carmel, Ind.; David W. Robertson, Poway, Calif.

[73] Assignee: Eli Lilly and Company, Indianapolis, Ind.

[21] Appl. No.: 936,684

[22] Filed: Aug. 27, 1992

[51] Int. Cl.$^6$ .................... A61K 31/48; C07D 457/00
[52] U.S. Cl. ........................................ 514/288; 546/69
[58] Field of Search ........................... 546/69; 514/288

[56] References Cited

U.S. PATENT DOCUMENTS

| | | | |
|---|---|---|---|
| 2,997,470 | 8/1961 | Pioch | 260/247.2 |
| 3,183,234 | 5/1965 | Garbrecht et al. | 260/285.5 |
| 3,228,944 | 1/1966 | Bernardi et al. | 260/285.5 |
| 3,580,916 | 5/1971 | Garbrecht | 260/285.5 |
| 4,180,581 | 12/1979 | Stadler | 546/69 X |
| 4,609,731 | 9/1985 | Jurgec et al. | 544/346 |
| 4,734,501 | 3/1988 | Marzoni | 546/69 |
| 4,902,691 | 2/1990 | Cohen et al. | 514/288 |
| 4,931,447 | 6/1990 | Foreman et al. | 514/288 |
| 4,970,314 | 11/1990 | Borner et al. | 544/346 |
| 5,043,341 | 8/1991 | Cohen et al. | 514/288 |

FOREIGN PATENT DOCUMENTS

| | | | |
|---|---|---|---|
| 717987 | 9/1965 | Canada. | |
| 789017 | 7/1968 | Canada. | |
| 125498 | 7/1967 | Czechoslovakia. | |
| 0082805 | 6/1983 | European Pat. Off. | 546/69 |
| 386411 | 4/1965 | Switzerland. | |
| 0579080 | 8/1976 | Switzerland | 546/69 |
| 0579566 | 9/1976 | Switzerland | 546/69 |
| 816273 | 7/1959 | United Kingdom. | |
| 982737 | 2/1965 | United Kingdom. | |
| 1227006 | 3/1971 | United Kingdom. | |
| 1345546 | 1/1974 | United Kingdom. | |

OTHER PUBLICATIONS

Derwent Abstracts 91-038417/06, abstracting EP 411494 (1991).
Derwent Abstracts 91-038418/06, abstracting EP 411495 (1991).
Chem. Abs., 54, 4925g (1960).
Derwent Abstracts 4840, abstracting Bel 603751 (1959).
Chem. Abs., 54, 14287g (1960).
Chem. Abs., 65, 3923b (1966).
Chem. Abs., 65, 3924b (1966).
Chem. Abs., 65, 3924f (1966).
Chem. Abs., 63, 13341b (1965).
Chem. Abs., 62, 4069b (1965).
Chem. Abs., 58, 557a (1963).
Chem. Abs., 58, 1501g (1963).
Derwent Astracts, 6972, abstracting Bel 625369 (1961).
Derwent Abstracts, 10,703, abstracting Bel 634886 (1962).
Derwent Abstracts, 7520, abstracting Bel 624577 (1961).
Floss et al., J. of Pharmaceutical Sciences, 62(5), 699–715 (1973).
The Pharmacological Basis of Therapeutics, 6th Ed., MacMillan Publishing Co., Inc., pp. 939–947 (1980).

Primary Examiner—Johann Richter
Assistant Examiner—Michael Hydorn
Attorney, Agent, or Firm—Joseph A. Jones; Douglas J. Taylor

[57] ABSTRACT

The present invention provides (8β)-N-substituted cyclo or bicycloalkyl-6-(substituted)-ergoline-8-carboxamides useful for occupying $5HT_2$ or $5HT_{1c}$ receptors in mammals. The invention also provides methods for treating a variety of disorders and conditions related to or affecting these receptors as well as pharmaceutical formulations of the compounds of the invention.

15 Claims, No Drawings

SUBSTITUTED CYCLO OR BICYCLOALKYLAMIDES OF (8β)-6-(SUBSTITUTED) ERGOLINES

BACKGROUND OF THE INVENTION

Foreman et al., U.S. Pat. No. 4,931,447, disclose (8β)-N-cycloalkyl-1-alkyl-6-(substituted)ergoline-8-carboxamides of the formula

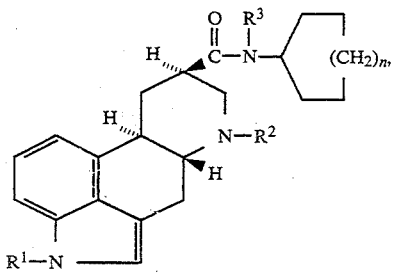

wherein:
$R^1$ is a $C_1$-$C_4$ alkyl;
$R^2$ is allyl or $C_1$-$C_4$ straight chain alkyl;
$R^3$ is hydrogen or $C_1$-$C_4$ straight chain alkyl;
$R^4$ is hydrogen, $C_1$-$C_4$ alkyl, hydroxy or $C_1$-$C_4$ alkoxy;
n is 0, 1, 2 or 3; and
the pharmaceutically acceptable acid addition salts thereof. The reference compounds are said to be useful for blocking 5HT$_2$ receptors in mammals having an excess of serotonin centrally or peripherally and, as such, are useful for treating hypertension, migraine, vasospasm, thrombosis, ischemia, depression, anxiety, sleep, appetite disorders, and the like.

Cohen et al., U.S. Pat. No. 4,902,691, disclose (8β)-N-heteroalkyl-1-alkyl-6-(substituted)ergoline-8-carboxamides of the formula

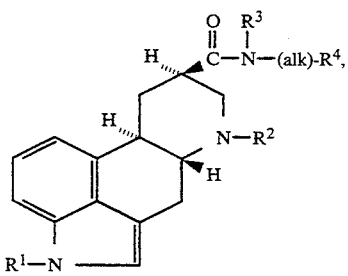

wherein
$R^1$ is a $C_{1-4}$ alkyl;
$R^2$ is allyl or $C_{1-4}$ straight chain alkyl;
$R^3$ is hydrogen or $C_1$-$C_4$ straight chain alkyl;
$R^4$ is pyridinyl or imidazolyl;
alkyl is a divalent organic radical derived from a straight or branched $C_1$-$C_5$ alkane; and the pharmaceutically acceptable acid addition salts thereof. Such reference compounds are said to be useful for blocking 5HT$_2$ receptors in mammals having an excess of serotonin centrally or peripherally and, as such, are useful for-treating the disease states noted above.

Garbrecht et all., U.S. Pat. No. 3,183,234, disclose octahydroindoloquinolines of the formula

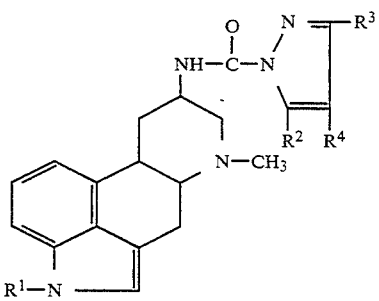

wherein:
$R^1$ is hydrogen, methyl, ethyl, isopropyl, allyl or propargyl;
$R^2$ and $R^3$ are hydrogen, methyl, ethyl, propyl, isopropyl, phenyl or halophenyl;
$R^4$ is hydrogen, an aliphatic radical containing 1 to 3 carbon atoms or halo, or $R^3$ and $R^4$, when taken together, represent a $C_3$-$C_4$ alkylene chain which together with the carbon atoms to which they are attached form a cycloaliphatic ring. The reference compounds are said to exhibit hypotensive and antiulcer activity.

Despite the progress of science as represented above, many mammals, both humans and animals, continue to be afflicted with one or more of the disease states noted above. Accordingly, the need continues for safer, more selective- drugs which can be used to treat such diseases.

As such, an object of the present invention is to provide substituted cyclo or bicycloalkylamides of (8β)-6-(substituted) ergolines which are useful for occupying the 5HT$_2$ or 5HT$_{1c}$ receptors in mammals. Such activity renders the present compounds useful for treating disease states such as obesity, appetite disorders (such as bulemia), obsessive-compulsive disorders, alcoholism, pain, sleep disorders ( such as sleep apnea), substance abuse, hypertension, thrombosis, bladder dysfunction, complications arising from atherosclerosis, migraine, vascular occlusive disease, vasospasm (both coronary and cerebral), ischemia, depression, anxiety, schizophrenia, sexual dysfunction and the like.

SUMMARY OF THE INVENTION

The present invention relates to a compound of the formula

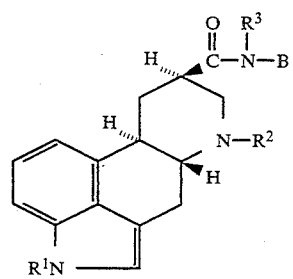

wherein:
$R^1$ is hydrogen, $C_1$-$C_4$ alkyl, —$CH_2$—($C_2$-$C_4$ alkenyl), benzyl, $C_3$-$C_8$ cycloalkyl, or substituted $C_3$-$C_6$ alkyl;
$R^2$ is allyl or $C_1$-$C_4$ alkyl;
B is

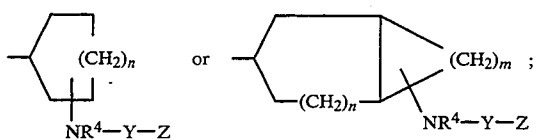

n is 0, 1 or 2;
m is 1, 2, 3, 4 or 5;

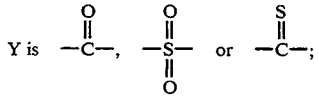

R³ and R⁴ are each independently hydrogen or C₁–C₄ alkyl;
Z is C₁–C₆ alkyl or C₃–C₈ cycloalkyl; and
the pharmaceutically acceptable acid addition salts thereof.

The present invention also provides pharmaceutical formulations comprising, and methods of using, the compounds of the invention.

DETAILED DESCRIPTION OF THE INVENTION

In the above formula, the term "$C_1$–$C_6$ alkyl" represents a straight or branched alkyl chain having from one to six carbon atoms. Typical $C_1$–$C_6$ alkyl groups include methyl, ethyl, n-propyl, isopropyl, n-butyl, sec-butyl, n-pentyl, n-hexyl and the like. The term "$C_{1-6}$ alkyl" includes within it the term "$C_1$–$C_4$ alkyl".

The term "—CH₂—(C₂–C₄ alkenyl)" represents a straight or branched primary or secondary alkenyl group having at least one carbon-carbon double bond. Typical —CH₂—(C₂–C₄ alkenyl) groups include allyl, 2-butenyl, 2-pentenyl and the like.

The term "$C_3$–$C_8$ cycloalkyl" refers to the saturated alicyclic rings of three to eight carbon atoms such as cyclopropyl, cyclobutyl, cyclopentyl, cyclohexyl, cyclooctyl and the like. Such term also encompasses saturated alicyclic rings of three to seven carbon atoms bonded to the rest of the molecule by an alkyl chain of one to four carbon atoms, provided the total number of carbon atoms in the alicyclic ring and connecting alkyl chain does not exceed eight. As such, "$C_3$–$C_8$ cycloalkyl" also refers to methylcyclopropyl, ethylcyclopropyl, propylcyclobutyl, methylcyclohexyl, ethylcyclohexyl and the like. The term "$C_3$–$C_8$ cycloalkyl" includes within it the term "$C_3$–$C_6$ cycloalkyl".

"Substituted $C_3$–$C_6$ cycloalkyl" represents a $C_3$–$C_6$ cycloalkyl group, as defined above, substituted with one or more $C_1$–$C_4$ primary or secondary alkyl groups on the carbon atoms of the alicyclic ring. The alkyl substituents present in this classification differ from the $C_1$–$C_4$ alkyl chain described above in that such substituents do not connect the alicyclic ring to the rest of the molecule. Typical members of this classification include 2-methylcyclopropyl, 2methylcyclopropylmethyl, 2-methylcyclobutyl, 2,3-dimethylcyclopentyl and the like.

While all of the compounds of the present invention are believed useful for occupying 5HT₂ and 5HT₁c receptors in mammals, certain of the compounds are preferred for such use. Preferred compounds of the present invention are those wherein R², B, n, m, Y and Z are as set forth above and R¹ is $C_1$–$C_4$ alkyl. Of these preferred compounds even more preferred are those compounds wherein R³ and R⁴ are both hydrogen. Of these even more preferred compounds especially preferred are those compounds wherein B is a cycloalkylamide moiety of the formula

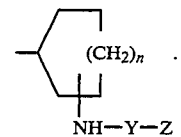

Preferred compounds among such especially preferred compounds are those compounds wherein R¹ is isopropyl, R² is methyl, n is 1, Y is

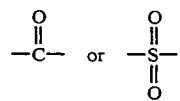

and, when n is 1, the —NH—Y—Z moiety is substituted at the 4-position of the resulting cyclohexane ring.

Of those even more preferred compounds, preferred compounds when B is a bicycloalkyl-amide moiety of the formula

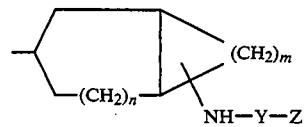

include those compounds wherein R¹ is isopropyl, R² is methyl, n is 0 or 1 (preferably 1), m is 3 or 4 (preferably 4); Y is $$-\overset{O}{\underset{\|}{C}}- \quad \text{or} \quad -\overset{O}{\underset{\underset{O}{\|}}{\overset{\|}{S}}}-$$

and, when n is i and m is 4, —NH—Y—Z is substituted as follows

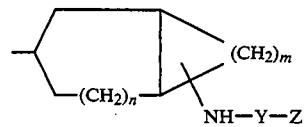

Other preferred aspects of the present invention will be noted hereinafter.

Compounds of the present invention are named as ergoline derivatives in which the trans(-) or 5R,10R configuration of the bridgehead hydrogens is specified. This is the same configuration as in the naturally-occurring 9,10-dihydro ergot alkaloids. In U.S. Pat. No. 3,580,916, a different naming system is used. The basic ring system is named as a 6aR, 10aR-4,6,6a, 7,8,9,10,10a-octahydroindolo [4,3 -f,g]quinoline. Illustratively, by the alternate naming system, 9,10-dihydrolysergic acid becomes 6aR, 10aR-7 -methyl-4,6,6a, 7,8,9,10,10a-octahydroindolo[4,3-f,g]quinoline-9β-carboxylic acid. Another equally valid name for dihydrolysergic acid is (8β)-6-methylergoline-8-carboxylic acid. The trivial name "ergoline" will be employed herein with the numbering system specified above for compounds of the invention.

While the configuration at asymmetric carbons 5, 8 and 10 in the above formula is set as 5β, 8β and 10α, generally speaking, compounds wherein B is a substituted cycloalkylamide group contain two additional asymmetric carbons. For example, 3-acetamidocyclohexylamide exists as two racemates, each racemate containing two enantiomers or stereoisomers. However, where the substituted cycloalkylamide possesses a plane of symmetry (for example, 4-acetylamidocyclohexylamide) mirror images turn out to be superimposable, and the compound actually exists in only two forms. These forms are designated as the cis form and the trans form, drawn for convenience in two dimensions as Ia and Ib.

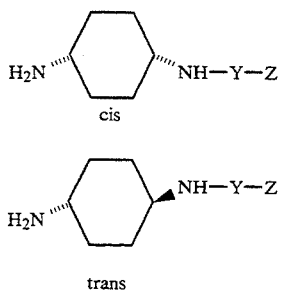

When an amide of an (8β)-1-alkyl-6-(substituted)ergoline-8-carboxylic acid is formed with a cis or trans 4-substituted cyclohexylamine, the product will be a single geometrical isomer. In general, the two amides in this instance will also be named, for the sake of simplicity, as cis and trans (4-substituted)-cyclohexylamides.

In addition, compounds wherein B is a bicycloalkylamide contain yet another two asymmetric carbons; namely, the bridgehead carbon atoms. For example, 4-acetylamido-bicyclo[4.4.0]decylamide contains 4 asymmetric carbon atoms denoted with asterisks as shown below.

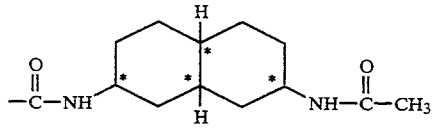

As such, the bicycloalkylamide compounds of the present invention can exist in many different stereochemical configurations including diasteromeric pairs, enantiomers, racemates as well as individual diasteromers and stereoisomers.

This invention contemplates all such stereochemical forms discussed above as useful for blocking $5HT_2$ or $5HT_{1c}$ receptors in mammals.

Pharmaceutically-acceptable acid addition salts of the compounds of the invention include salts derived from inorganic acids such as hydrochloric acid, nitric acid, phosphoric acid, sulfuric acid, hydrobromic acid, hydroiodic acid, phosphorous acid and the like, as well as salts derived from organic acids such as aliphatic mono- and dicarboxylic acids, phenyl-substituted alkanoic acids, alkandioic acids, aromatic acids, aliphatic and aromatic sulfonic acids and the like. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, caprylate, acrylate, formate, isobutyrate, caprate, heptanoate, oxalate, malonate, succinate, suberate, sebacate, fumarate, maleate, mandelate, butyne-1,4-dioate, hexyne-1,6-dioate, benzoate, chlorobenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and like salts.

The compounds of the present invention may be prepared by a variety of procedures well known to those of ordinary skill in the art. The preferred method of preparing compounds of Formula I is that of acylating the appropriate aminocycloalkylamide or aminobicycloalkylamide as represented in Reaction Scheme I.

Reaction Scheme I

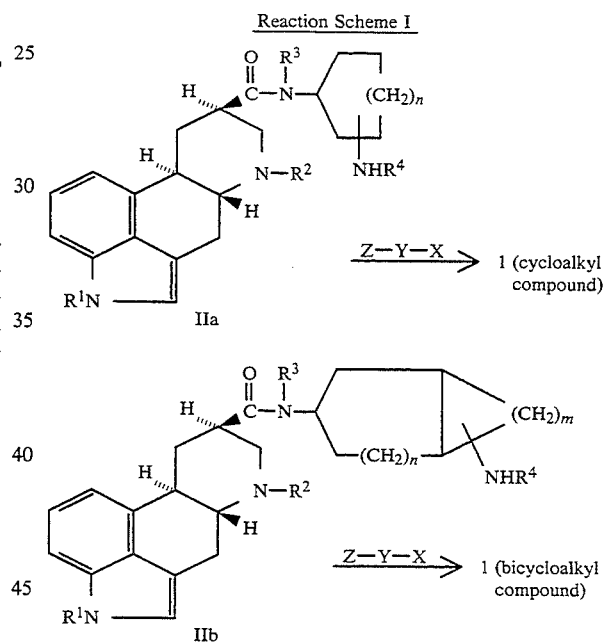

where X is iodo, bromo, or preferably chloro. The reaction is best carried out by mixing intermediate IIa or IIb with reagent Z—Y—X in a non-reactive solvent, such as tetrahydrofuran, preferably in the presence of a non-reactive acid scavenger, such as pyridine or triethylamine. It is preferred that equimolar or slight molar excesses of Z—Y—X and the acid scavenger be employed to maximize the yield, though other ratios are operative. The reaction is accomplished at temperatures from about 0° C. up to the boiling point of the reaction mixture. However, at ambient temperature (20°–25° C.), the reaction is usually complete in 2–8 hours. The resulting product is isolated by standard procedures and purified by known methods such as crystallization or chromatography.

Other methods for preparing final product I, as well as intermediates IIa and IIb are as follows.

Preferably, for compounds wherein $R^2$ is methyl, dihydrolysergic acid is converted to the alkali metal salt and then to the ($C_1$–$C_4$ alkyl)formate derivative. This compound is finally reacted with the appropriate amine to provide a compound or intermediate of the invention. This reaction is represented by the following scheme:

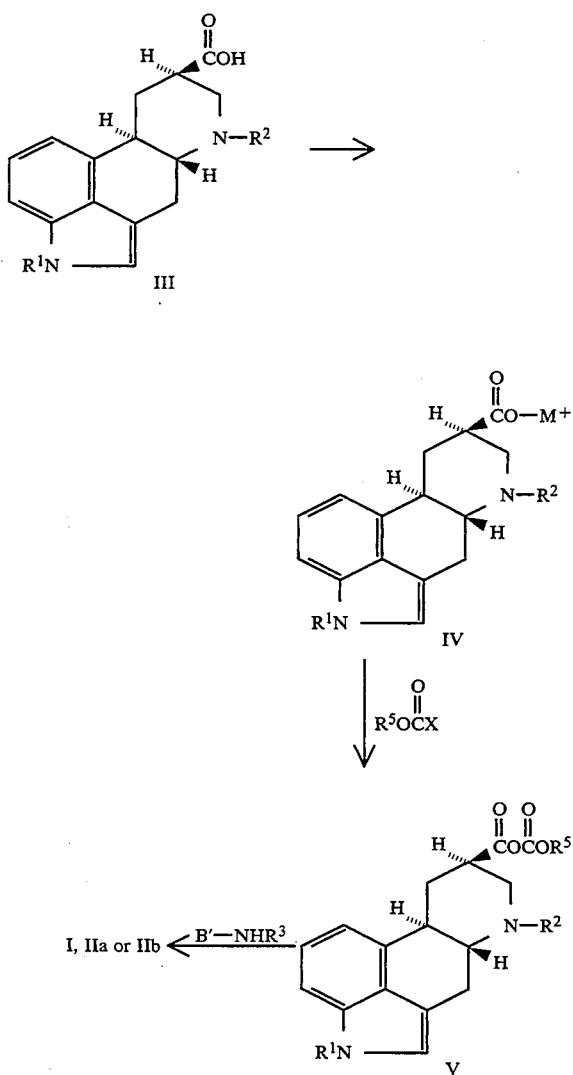

wherein $R^1$, $R^2$ and X are as defined above, $R^5$ is a $C_1$–$C_4$ alkyl, such as methyl, ethyl or preferably isobutyl, $R^3$ is hydrogen or $C_1$–$C_4$ alkyl, B' is

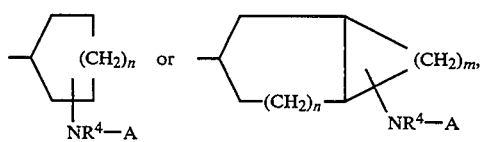

$R^4$ is hydrogen or $C_1$–$C_4$ alkyl, A is hydrogen or —Y—Z (where Y and Z are as defined above), n is 0, 1 or 2, m is 1, 2, 3, 4 or 5, and M is an alkali metal cation.

The reaction can be carried out by combining the dihydrolysergic acid derivative III with about an equimolar quantity to slight excess of the base containing an alkali metal in a mutual solvent such as tetrahydrofuran, diethyl ether, dichloromethane, dioxane, dimethylsulfoxide, N,N-dimethylformamide (DMF), benzene, toluene, and the like. Commonly used bases include sodium or potassium hydride, sodium carbonate and especially potassium carbonate. This mixture is typically heated to form the alkali metal salt intermediate IV. The mixture is next cooled and an equimolar to slight excess of a $C_{1-4}$ alkyl haloformate is added to the reaction mixture. After sufficient time to form the ($C_{1-4}$ alkyl)formate intermediate V, typically approximately five to about 30 minutes, at least one equivalent of the desired cyclo or bicycloalkylamine is added to the reaction mixture. Generally, the reaction is substantially complete after about two to about 200 hours when carried out at a temperature of about $-40°$ to about $50°$ C., preferably from about $-20°$ to about $25°$ C. The product of the reaction my be isolated by simply removing the reaction solvent, for instance by evaporation under reduced pressure. More typically, the reaction mixture containing the free base of the desired compound may be combined with water, and the product collected by filtration or extracted into a water immiscible solvent. The product thus isolated can be further purified if desired by any of several well known techniques.

If the desired final product is not a 9,10-dihydrolysergic acid amide, that is, not a $(8\beta)$-6-methylergoline-8-carboxamide, but is a 6-ethyl, 6-n-propyl, 6-n-butyl, 6-allyl or the like derivative, the replacement of the 6-methyl group must take place prior to the amination procedure described above. For these compounds, it is preferable to use a lower alkyl (such as methyl or ethyl) ester of a 9,10-dihydrolysergic acid. Replacement of the 6-methyl group with ethyl, n-propyl, n-butyl, allyl or the like, can be carried out by the procedure of U.S. Pat. No. 4,166,182, whereby the N-methyl group is reacted with cyanogen bromide to form an N-cyano derivative. The cyano group can be removed by hydrogenation using zinc dust and hydrochloric acid. Alternatively, basic hydrolysis can be used. Either procedure provides a secondary amine group at the 6-position, but also a free $8\beta$-carboxylic acid since the hydrolysis also saponifies the $8\beta$-lower alkyl ester group. The 6-position is then alkylated or allylated using standard conditions followed by amidation with the desired cyclo or bicycloalkylamine. Such procedure is graphically illustrated by the following reaction scheme:

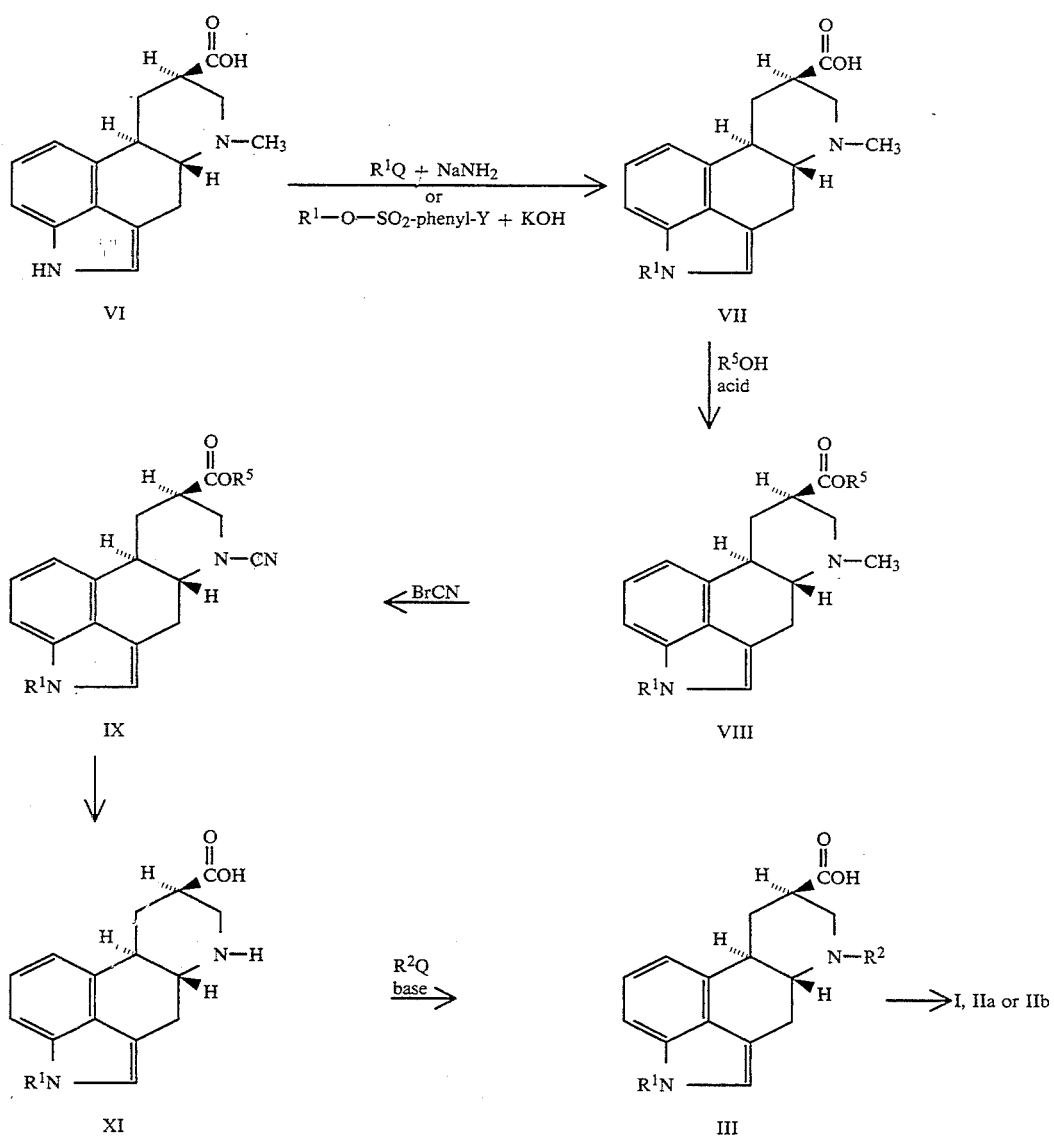

wherein $R^1$ and $R^2$ are as defined above, $R^s$ is $C_1$–$C_4$ alkyl and Q is a good leaving group such as halo or a sulfonate derivative.

More specifically, in the above reaction scheme, 9,10-dihydrolysergic acid (VI) is alkylated on the indole nitrogen with a $C_1$–$C_4$ alkyl halide using sodamide to create the reactive anion, or preferably using an aryl sulfonate of the structure $R^1$—O—$SO_2$-phenyl-Y, wherein Y is hydrogen, 4-$CH_3$, 4-Br or 4-$NO_2$, in the presence of potassium hydroxide in DMSO. The N-1 product (VII) is then esterified with a lower alkanol $R^5OH$ (a $C_1$–$C_2$ alkanol preferably) to yield the ester (VIII). This intermediate is then reacted with BrCN using standard procedures to replace the methyl group and form a 6-cyano derivative (IX). Removal of the cyano group under the preferred basic conditions yields a (8β)-6-methylergoline-8-carboxylic acid (XI). The ring nitrogen at $N^6$ is then realkylated with a $C_1$–$C_4$ alkyl halide or allyl halide in the presence of base under standard conditions to provide intermediates of Formula III. Finally, the acid is converted to the amide with the desired cyclo or bicycloalkylamine by the procedures herein described, such as with a coupling reagent such as N,N'-dicyclohexylcarbodiimide or carbonyldiimidazole to provide the compounds of this invention.

It might seem Sisyphean to realkylate at $N^6$ with a methyl group since that group is present in the 9,10 - dihydrolysergic acid starting material. However, the process would enable one to insert a radio-labeled ($^{14}C$ or $^3H$) methyl group into the compound for metabolic or receptor binding studies.

The compounds of the present invention may also be prepared by the reaction of a 1-alkyl-6-(substituted)-ergoline-8-hydrazide with the desired cyclo or bicycloalkylamine under conditions well known to those of ordinary skill in the art. This reaction may be represented by the following scheme:

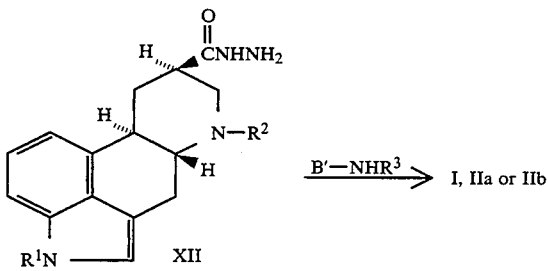

wherein $R^1$, $R^2$, $R^3$ and B' are as defined above.

According to this procedure, the hydrazide starting material XII is dissolved in an aqueous acidic solution and the resulting mixture is cooled to a temperature in the range of about 0° C. to about 20° C. Typical acids suitable for use in this step of the process include the hydrohalic acids, such as hydrobromic acid and hydroiodic acid, and especially hydrochloric acid. To this mixture is added either sodium nitrite or sodium periodate, typically in an excess amount, and the mixture is made basic with a suitable base such as the inorganic bases, especially sodium bicarbonate. The intermediate formed by this reaction is isolated by extraction with a water immiscible organic solvent, and an equimolar, to preferably an excess, of the desired cyclo or bicycloalkylamine is then combined with the solution containing the intermediate. The reaction is substantially complete within about one to 24 hours when conducted at a temperature in the range of about 0° C. to about 100° C., more preferably within about four to 12 hours when conducted at a temperature in the range of about 5° C. to about 20° C. The product is then isolated, typically by decanting or evaporating the volatile constituents under vacuum. The isolated product may then be further purified, if desired, by standard procedures.

The compounds of the present invention may also be prepared by the direct coupling of a (8β)-1-alkyl-6-(substituted)ergoline-8-carboxylic acid derivative with an appropriate cyclo or bicycloalkylamine in the presence of a coupling reagent to provide the corresponding (8β)-1-alkyl-6-(substituted)ergoline-8-carboxamide.

This reaction may be represented by the following scheme:

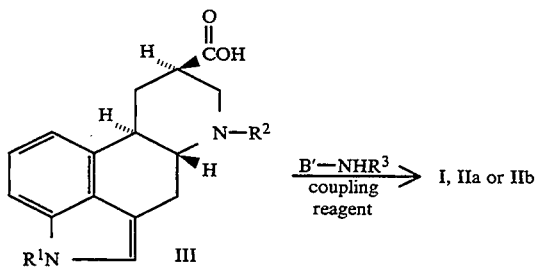

wherein $R^1$, $R^2$ $R^3$ and B' are as defined above.

This reaction necessitates the use of a coupling reagent, for example any of the type of coupling reagents commonly employed in the synthesis of peptides. Examples of such coupling reagents include the carbodiimides such as N,N'-dicyclohexylcarbodiimide, N,N'-diisopropylcarbodiimide, or N,N'-diethyl-carbodiimide; the imidazoles such as carbonyldiimidazole; as well as reagents such as 1-hydroxybenzotriazole mesylate or N-ethoxycarbonyl-2-ethoxy-1,2-dihydroquinoline (EEDQ). The direct coupling of an (8β)-1-alkyl-6-(substituted)ergoline-8-carboxylic acid III and a cyclo or bicycloalkylamine is carried out by adding about an equimolar quantity of the amine starting material to a solution of the carboxylic acid in the presence of an equimolar quantity to slight excess of the coupling reagent. The reaction generally is carried out in an inert organic solvent such as dichloromethane, tetrahydrofuran (THF) or N,N-dimethylformamide (DMF), and is typically complete within about twenty-four hours when conducted at a temperature of about 0° to about 30° C. The product is then typically isolated by filtration. The (8β)-1-alkyl-6-(substituted)ergoline-8-carboxamide thus formed can be further purified, if needed, by any of several routine methods, including crystallization from common solvents, chromatography over solid supports such as silica or alumina, and related purification techniques.

Amide formation can also be accomplished by converting acid III to the corresponding acid chloride followed by reaction with the desired cyclo or bicycloalkylamine. The acid halide of an (8β)-1-alkyl-6-(substituted)ergoline-8-carboxylic acid is generated from the acid through the use of a suitable reagent such as thionyl chloride, oxalyl chloride, or phosphorus oxychloride in an inert solvent such as dichloromethane, tetrahydrofuran (THF) or N,N-dimethylformamide (DMF). An equimolar quantity to slight excess of the reagent is used, and acid halide formation is typically complete within about twenty-four hours when conducted at a temperature of about $-25°$ to about 30° C. The cyclo or bicycloalkylamine is then added, preferably along with an acid scavenger such as an alkali metal carbonate, triethylamine, or pyridine. Generally, amide formation is substantially complete after about two to about 200 hours when conducted at a temperature of about $-40°$ to about 50° C., preferably from about $-20°$ to about 25° C. The product of the reaction may be isolated by simply removing the reaction solvent, for instance by evaporation under reduced pressure. More typically, the reaction mixture containing the free base of the desired compound my be combined with water, and the product collected by filtration or extracted into a water immiscible solvent. The product thus isolated can be further purified if desired by any of several well known techniques.

The preparation of the ergoline compounds which are intermediates to the compounds of the present invention is well known to those of ordinary skill in the art. According to one art-known procedure, dihydrolysergic acid is first alkylated on the N-1 nitrogen atom with an alkyl halide in the presence of a base. Liquid ammonia is a convenient solvent with sodamide the preferred base. An alternate alkylation procedure whereby a sulfonate derivative is used in the presence of an alkali metal hydroxide is more fully described in U.S. Pat. No. 4,734,501. According to this procedure, an aryl-sulfonate of the structure $R^1$—O—SO$_2$-phenyl-Y, wherein Y is hydrogen, 4-CH$_3$, 4-Br or 4-NO$_2$ is reacted with an ergoline-8-carboxylic acid in a suitable solvent, conveniently DMSO, in the presence of base, preferably sodium or potassium hydroxide.

To synthesize compounds wherein the 6-position is other than methyl, that is, the compound possesses a 6-allyl, 6-ethyl, 6-n-propyl, 6-n-butyl substituent, or the like derivative, the replacement of the 6-methyl group will take place prior to amidation as described above.

In any of the latter reactions used to prepare cycloalkylamide IIa, or bicycloalkylamide IIb, a large molar excess of the diamine reactant and dilute reaction conditions are preferred to prevent formation of dimeric material.

The pharmaceutically acceptable acid addition salts of the invention are typically formed by reacting an amide of the invention with an equimolar or excess amount of acid. The reactants are generally combined in a mutual solvent such as diethyl ether or benzene, and the salt normally precipitates out of solution within about one hour to 10 days, and can be isolated by filtration.

The following Examples further illustrate the compounds of the present invention and methods of their synthesis. The Examples are not intended to limit the scope of the invention in any respect and should not be so construed. Where structures were confirmed by proton nuclear magnetic resonance or mass spectral analysis, the compound is so designated by "NMR" and/or "MS", respectively.

PREPARATION 1

(8$\beta$)-N-(trans-4-aminocyclohexyl)-1-isopropyl -6-methylergoline-8-carboxamide To a solution of 10.07 g of (8$\beta$)-1-isopropyl-6-methylergoline-8-carboxylic acid in 300 ml of dimethylformamide were added 5.5 g of 1,1'-carbonyldiimidazole. After stirring at room temperature for 3 hours, this solution was added to a solution of 36.9 g of trans-1,4-diaminocyclohexane in 600 ml of dimethylformamide; the addition was made dropwise over a period of 3.5 hours. After the addition was complete, the reaction mixture was allowed to stir at room temperature overnight. The solution was poured into 4 liters of ice and the aqueous solution extracted 8 times with 500 ml each of methylene chloride. The combined organic extracts were washed three times with water, one time with a saturated sodium chloride solution, dried over sodium sulfate, and then concentrated in vacuo to provide 12.5 g of title compound as a yellow solid. A portion of this free base material was treated with p-toluenesulfonic acid in ethyl acetate/ethanol to provide the ditosylate salt, m.p. 236°–239° C. NMR, MS.

EXAMPLE 1

(8$\beta$)-N-(trans-4-acetamidocyclohexyl)-1-isopropyl-6-methylergoline-8-carboxamide To a solution of 620 mg of (8$\beta$)-N-(trans-4-aminocyclohexyl)-1-isopropyl-6-methylergoline-8-carboxamide in 100 ml of dry tetrahydrofuran were added 222 $\mu$l of triethylamine. The solution was cooled by means of an external ice bath and 118 $\mu$l of acetyl chloride were added in dropwise fashion. The mixture was stirred at room temperature under a nitrogen atmosphere for 2.5 hours. The reaction mixture was concentrated in vacuo and ethyl acetate, water, and 2N sodium hydroxide were added. The layers were separated and the aqueous layer extracted an additional three times with ethyl acetate and six times with methylene chloride. The combined organic layers were washed twice with water, once with a saturated sodium chloride solution, dried over sodium sulfate and concentrated in vacuo to provide 690 mg of a pale yellow solid. This material was crystallized from tetrahydrofuran/ethanol/hexanes to provide 259 mg of title product as a tan powder, m.p. >280° C. Analytical high pressure liquid chromatography indicated the material was 97.9% pure. NMR, MS Analysis for $C_{27}H_{38}N_4O_2$: Calc.: C, 71.97; H, 8.50; N, 12.43; Found: C, 71.66, H, 8.41; N, 12.21.

EXAMPLE 2

(8$\beta$)-N-(trans-4-methylsulfonamidocyclohexyl)-1-isopropyl-6-methylergoline-8-carboxamide maleate The title product was prepared in the same manner as described in Example 1, above, from 750 mg of the aminocyclohexylamide and 149$\mu$l of methanesulfonyl chloride. The maleate salt was prepared by dissolving the resulting free base material in ethyl acetate/ethanol, adding 1.05 equivalents of maleic acid in ethyl acetate, heating on a steam bath until a precipitate formed, cooling, and recovering the title product (850 mg) as a white powder, m.p. 201°–206° C. (decomposition). Analytical high pressure liquid chromatography indicated the material was 100% pure. NMR, MS.

Analysis for $C_{26}H_{38}N_4O_3S$: Calc.: C, 59.78; H, 7.02; N, 9.30; Found: C, 58.74; H, 7.08; N, 8.75.

DESCRIPTION OF USE FOR THE COMPOUNDS

As noted above, the compounds of Formula I are useful for occupying $5HT_2$ and $5HT_{1c}$ receptors in mammals having an excess of serotonin centrally or peripherally. As such, this invention also provides a method of occupying $5HT_2$ or $5HT_{1c}$ receptors which comprises administering to a mammal having an excess of serotonin centrally or peripherally a $5HT_2$ or $5HT_{1c}$ occupying dose of a compound of the invention. The instant method is useful in treating disease states associated with dysfunction in serotonergic systems involving the 2 or 1C receptors such as obesity, appetite disorders (such as bulemia), obsessive-compulsive disorders, alcoholism, pain, sleep disorders (such as sleep apnea), substance abuse (e.g., cocaine, heroin, amphetamines, etc.), bladder dysfunction, hypertension, thrombosis, complications arising from atherosclerosis, vascular occlusive disease, migraine, vasospasm (both coronary and cerebral), ischemia, depression, anxiety, schizophrenia, and sexual dysfunction.

In carrying out the methods of the invention, a compound of the invention is administered orally or parenterally (for example, intravenously, subcutaneously or transdermally) to a mammal with an excess of circulatory serotonin in which mammal it is desirable to occupy $5HT_2$ or $5HT_{1c}$ receptors in order to alleviate symptoms attributable to excessive serotonin levels such as migraine or depression. A preferred method of parenteral administration entails the use of a water soluble salt of the drug dissolved in an isotonic salt solution and then administered by the intravenous route. For oral administration, a pharmaceutically acceptable salt of the drug is mixed with standard pharmaceutical excipients such as starch and loaded into capsules or made into tablets, each containing about 0.1 to about 100 mg of active drug. Dosage levels of from about 0.01–1000 mg/kg are effective in occupying $5HT_2$ or $5HT_{1c}$ receptors. Thus, the oral dosage would be administered approximately 2–4 times per day, giving a daily dosage range of about 0.003 to about 10.0 mg/kg per day.

The following experiments were conducted to demonstrate the ability of the compounds of this invention to affect radioligand binding to five subtypes of serotonin receptors. The general procedure utilized herein is set forth by Wong et al., *Life Sciences*, 46, 231 (1990).

Bovine choroid plexus and brain tissues from male Sprague-Dawley rats were homogenized in 9 volumes of 0.32M sucrose. After centrifugation at 1000×g for 10 minutes and then at 17,000×g for 20 minutes, a crude synaptosomal fraction was sedimented. The pellet was suspended in 100 volumes of 50 mM Tris-HCl, pH incubated at 37° C. for 10 minutes, and centrifuged at 50,000×g for 10 minutes. The process was repeated, and the final pellet of membrane was suspended in ice-chilled 50 mM Tris-HCl buffer, pH Binding of $^3$H-mesulergine to the $5HT_{1c}$ receptor and other serotonergic $^3$H-ligands to subtypes of 5HT receptors [3H-8-hydroxy-2-(di-n-propylamino)tetralin to $5HT_{1D}$; $^3$H-serotonin to $5HT_{1B}$ and $5HT_{1D}$; and $^3$H-ketanserin to $5HT_2$ receptors] was performed according to the method described in the above reference. Briefly, membranes isolated from bovine choroid plexus (for $5HT_{1c}$) or rat brain were incubated at 25° C. for 30 minutes in 2 ml of 50 mM Tris-HCl, pH 7.4; 10 mM pargyline, 0.6 mM ascorbic acid; 5 mMCaCl$_2$; and 2 nM $^3$H-mesulergine or other tritiated ligand. Binding was terminated by filtering samples under reduced pressure through glass fiber (GFB) filters. The filters were washed 3 times with 5 ml of ice cold buffer and placed in scintillation vials with 10 ml of PCS (Amersham/-Searle) scintillation fluid. Radioactivity was measured with a liquid scintillation spectrometer. Serotonin at 10 $\mu$M also included in separate samples to determine specific binding, which accounted for 90-70 percent of total binding.

The results of the evaluation of compounds of this invention from these experiments are set forth below in Table I. In the Table, columns 2–5 provide the nanomolar (nM) concentration of test compound needed to inhibit radioligand binding by 50% for each of the indicated receptors.

TABLE 1

AFFINITIES OF COMPOUNDS OF FORMULA I FOR SUBTYPES OF SEROTONIN RECEPTORS
Inhibition of Radioligand Binding to 5HT

| Receptor* | Compound | | | | |
|---|---|---|---|---|---|
| | 1A | 1B | 1C | 1D | 2 |
| Example 1 | 2309 | >1000 | 18 | 198 | 31 |
| Example 2 | 2650 | 489 | 22 | 276 | 23 |

*IC50 IN nM(NANOMOLAR OR $10^{-9}$ M)

The compounds of the present invention are preferably formulated prior to administration. Therefore, yet another embodiment of the present invention is a pharmaceutical formulation comprising a compound of the invention and a pharmaceutically acceptable carrier, diluent or excipient therefor.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), ointments containing, for example, up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calciumphosphate, alginates, tragacanth, gelatin, calcium silicate, microcrystalline cellulose, polyvinylpyrrolidone, cellulose, water syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention my be formulated so as to provide quick, sustained or delayed release of the active ingredient after administration to the patient by employing procedures well known in the art.

The compositions are preferably formulated in a unit dosage form, each dosage containing from about 5 to about 500 mg, more usually about 25 to about 300 mg, of the active ingredient. The term "unit dosage form" refers to physically-discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

FORMULATION 1

Hard gelatin capsules are prepared using the following ingredients:

| | Quantity (mg/capsule) |
|---|---|
| 8β-N-[3-(2-methylbutylsulfonamido)-cyclopentyl-1-isopropyl-6-methylergoline-8-carboxamide | 250 |
| starch, dried | 200 |
| magnesium stearate | 10 |
| Total | 460 mg |

The above ingredients are mixed and filled into hard gelatin capsules in 460 mg quantities.

FORMULATION 2

A tablet is prepared using the ingredients below:

| | Quantity (mg/tablet) |
|---|---|
| 8β-N-(2-ethylsulfonamido)cyclopentyl-1-isopropyl-6-methylergoline-8-carboxamide | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

FORMULATION 3

An aerosol solution is prepared containing the following components:

|  | Weight % |
| --- | --- |
| 8β-N-(4-butanamidocycloheptyl)-1-isopropyl-6-methylergoline-8-carboxamide | 0.25 |
| ethanol | 29.75 |
| Propellant 22 (chlorodifluoromethane) | 70.00 |
| Total | 100.00 |

The active compound is mixed with ethanol and the mixture added to a portion of the propellant 22, cooled to −30° C., and then transferred to a filling device. The required amount is then fed to a stainless steel container and diluted with the remainder of the propellant. The valve units are then fitted to the container.

FORMULATION 4

Tablets each containing 60 mg of active ingredient are made as follows:

| 8β-N-methyl-N-(cis-4-propanamidocyclohexyl-1-isopropyl-6-methylergoline-8-carboxamide | 60 mg |
| --- | --- |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION 5

Capsules each containing 80 mg of medicament are made as follows:

| (8β)-N-(3-butylsulfonamidocycloheptyl-1-isopropyl-6-n-propylergoline-8-carboxamide maleate | 80 mg |
| --- | --- |
| starch | 59 mg |
| microcrystalline cellulose | 59 mg |
| magnesium stearate | 2 mg |
| Total | 200 mg |

The active ingredient, cellulose, starch and magnesium stearate are blended, passed through a No. 45 mesh U.S. sieve, and then filled into hard gelatin capsules in 200 mg quantities.

FORMULATION 6

Suppositories each containing 225 mg of active ingredient may be made as follows:

| (8β)-N-(3-acetamidocyclopentyl)-1-isopropyl-6-methylergoline-8-carboxamide | 225 mg |
| --- | --- |
| saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions each containing 50 mg of medicament per 5 ml dose are made as follows:

| (8β)-N-(3-methanesulfonamidocyclopentyl)-1-isopropyl-6-methylergoline-8-carboxamide | 50 mg |
| --- | --- |
| sodium carboxymethyl cellulose | 50 mg |
| syrup | 1.25 ml |
| benzoic acid solution | 0.10 ml |
| flavor | q.v. |
| color | q.v. |
| purified water to total | 5 ml |

The medicsanent is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

FORMULATION 8

An intravenous formulation may be prepared as follows:

| (8β)-N-(trans-4-propanamidocyclohexyl-1-isopropyl-6-methylergoline-8-carboxamide hydrochloride | 100 mg |
| --- | --- |
| isotonic saline | 1000 ml |

The solution of the above ingredients is administered intravenously at a rate of 1 ml per minute to a subject in need of treatment for sexual dysfunction.

We claim:

1. A compound of the formula

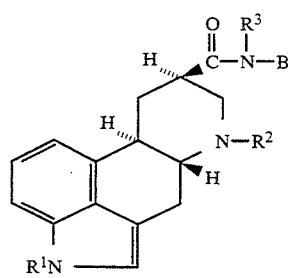

wherein:
R[1] is hydrogen, $C_1$-$C_4$ alkyl, —$CH_2$—($C_2$-$C_4$ alkenyl), benzyl, $C_3$-$C_8$ cycloalkyl, or substituted $C_3$-$C_6$ cycloalkyl;
R[2] is allyl or $C_1$-$C_4$ alkyl;
B is

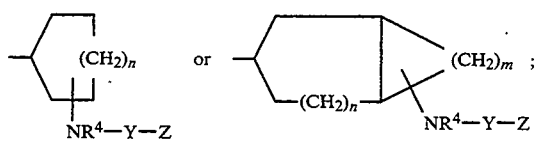

n is 0, 1 or 2;
m is 1, 2, 3, 4 or 5;

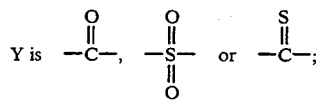

$R^3$ and $R^4$ are each independently hydrogen or $C_1$-$C_4$ alkyl;
Z is $C_1$-$C_6$ alkyl or $C_3$-$C_8$ cycloalkyl; and,
the pharmaceutically acceptable acid addition salts thereof.

2. A compound of claim 1 wherein B is

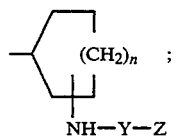

where n, Y and Z are as defined in claim 1.

3. A compound of claim 2 wherein $R^2$ is methyl.
4. A compound of claim 3 wherein n is 1.
5. A compound of claim 4 wherein Z is methyl.
6. A compound of claim 5 wherein $R^1$ is isopropyl.
7. The compound of claim 6 which is (8β)-N-(trans-4-acetamidocyclohexyl)-1-isopropyl-6-methylergoline-8-carboxamide or a pharmaceutically acceptable salt thereof.
8. The compound of claim 6 which is (8β)-N-(trans-4-methylsulfonamidocyclohexyl)-1-isopropyl-6-methylergoline-8-carboxamide or a pharmaceutically acceptable salt thereof.
9. A pharmaceutical formulation comprising a compound of claim 1 associated with a pharmaceutically acceptable carrier, diluent or excipient therefor.
10. A pharmaceutical formulation of claim 9 wherein B is

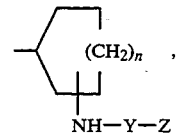

where n, Y and Z are as defined in claim 9.

11. A formulation of 10 wherein $R^2$ is methyl.
12. A formulation of 11 wherein n is 1.
13. A formulation of 12 wherein $R^1$ is isopropyl.
14. The formulation of claim 13 wherein the compound employed is (8β)-N-(trans-4-acetamidocyclohexyl)-1-isopropyl-6-methylergoline-8-carboxamide or a pharmaceutically acceptable salt thereof.
15. The formulation of claim 13 wherein the compound employed is (8β)-N-(trans-4-methylsulfonamidocyclohexyl) -1-isopropyl-6-methylergoline-8-carboxamide or a pharmaceutically acceptable salt thereof.

* * * * *